US012305694B2

(12) United States Patent
Schindlbeck et al.

(10) Patent No.: US 12,305,694 B2
(45) Date of Patent: May 20, 2025

(54) ROLLING ELEMENT ASSEMBLY FOR ADJUSTMENT OF TELESCOPIC ARM

(71) Applicant: AGFA NV, Mortsel (BE)

(72) Inventors: Guenther Schindlbeck, Munich (DE); Johannes Hoelzl, Munich (DE)

(73) Assignee: Agfa NV, Mortsel (BE)

( * ) Notice: Subject to any disclaimer, the term of this patent is extended or adjusted under 35 U.S.C. 154(b) by 422 days.

(21) Appl. No.: 17/777,816

(22) PCT Filed: Nov. 16, 2020

(86) PCT No.: PCT/EP2020/082221
§ 371 (c)(1),
(2) Date: May 18, 2022

(87) PCT Pub. No.: WO2021/099250
PCT Pub. Date: May 27, 2021

(65) Prior Publication Data
US 2022/0412396 A1     Dec. 29, 2022

(30) Foreign Application Priority Data

Nov. 20, 2019   (EP) ..................... 19210371

(51) Int. Cl.
*F16C 1/04*   (2006.01)
(52) U.S. Cl.
CPC ..................... *F16C 1/04* (2013.01)
(58) Field of Classification Search
CPC .................. F16C 1/04; F16C 3/035
See application file for complete search history.

(56) References Cited

U.S. PATENT DOCUMENTS

| | | | |
|---|---|---|---|
| 3,776,500 A | 12/1973 | Foderaro | |
| 4,041,320 A * | 8/1977 | Amor, Jr. | A61B 6/4464 378/197 |
| 5,020,323 A * | 6/1991 | Hurlimann | F16M 11/28 414/718 |
| 6,524,012 B1 * | 2/2003 | Uchman | B60B 27/0084 384/903 |
| 9,380,866 B1 | 7/2016 | Davis | |

(Continued)

FOREIGN PATENT DOCUMENTS

| | | |
|---|---|---|
| DE | 10019576 A1 | 10/2001 |
| EP | 0068930 A2 | 1/1983 |

OTHER PUBLICATIONS

European Patent Office, International Search Report in International Patent Application No. PCT/EP2020/082221, mailed Jan. 16, 2021, 4 pp.

(Continued)

*Primary Examiner* — Monica E Millner
(74) *Attorney, Agent, or Firm* — Leydig, Voit & Mayer, Ltd.

(57) ABSTRACT

This invention is related to a rolling element assembly that can be integrated into a telescopic arm segment assembly, comprising a pair of auto-adjusting rolling elements, that assume their optimal mounting position between two concentric telescopic arm segments, as they are spring-loaded by the presence of a connecting spring element. The final adjustment and fixation of the rolling elements (comprising each a pair of rollers) can then be subsequently be performed with high precision.

8 Claims, 4 Drawing Sheets

(56) References Cited

U.S. PATENT DOCUMENTS

| | | | | |
|---|---|---|---|---|
| 9,587,411 | B2* | 3/2017 | Bach | F16B 2/18 |
| 10,512,334 | B1* | 12/2019 | Koh | A47C 3/30 |
| 10,661,592 | B2* | 5/2020 | Lucio | F21V 21/32 |
| 2006/0109955 | A1* | 5/2006 | Boomgaarden | A61B 6/4464 |
| | | | | 378/197 |
| 2012/0207281 | A1 | 8/2012 | Kim | |
| 2015/0211250 | A1 | 7/2015 | Bach | |
| 2016/0052761 | A1* | 2/2016 | Berry | B66F 11/046 |
| | | | | 384/46 |

OTHER PUBLICATIONS

European Patent Office, Written Opinion in International Patent Application No. PCT/EP2020/082221, mailed Jan. 16, 2021, 5 pp.

* cited by examiner

ROLLING ELEMENT ASSEMBLY FOR ADJUSTMENT OF TELESCOPIC ARM

CROSS-REFERENCE TO RELATED APPLICATIONS

This patent application is the U.S. national phase of copending International Patent Application No. PCT/EP2020/082221, filed Nov. 16, 2020, which claims the benefit of European Patent Application No. 19210371.1, filed Nov. 20, 2019.

TECHNICAL FIELD

The present invention relates to a rolling element assembly that can be fitted into a telescopic arm, and more specifically between the interspacing between two concentric telescopic arm segments in order to provide a sliding action of a first segment with respect to a second segment. More specifically, the invention can be applied in the field of mechanical telescopic arms that can be used in X-ray imaging modalities.

BACKGROUND OF THE INVENTION

High-precision telescopic arms are used in various applications, and serve the purpose of providing a solid and extendible support for heavy appliances or devices. While mechanical stands with telescopic arms provide solid support for heavy objects, they are capable of maintaining the flexibility for an operator to move the mounted appliance at the end of such arm along a linear path. When used in combination with other parts such as rotating joints or axles, telescopic arms allow movements with much more degrees of freedom, and thus can offer quite some movement flexibility.

Telescopic arms are known in the art and more specifically in the field of X-ray devices as illustrated in U.S. Pat. No. 3,776,500A. Telescopic and extendable arms are typically constructed as columnar structures comprising concentrically positioned tubular sections nested one within another. Each of the sections, except the innermost section, has a plurality of ways extending along its interior. Each of the sections, except the outermost section comprises a metallic extrusion which carries a plurality of guide bearings on its exterior to cooperate with the ways. An adjustment means is associated with each of the guide bearings whereby the pre-load normal force between the nested and nesting sections may be adjusted. The example above limits the movement of the telescopic arm to vertical movements.

However, when telescopic arms have to operate when positioned horizontally or under a variety of angles, it is clear that the presence of bearings or rollers become required ensuring the relative movement between subsequent segments. The presence of rollers or bearings is advantageous in that they can provide smooth and almost frictionless relative movement between the different segments. In the art, different constructions are described that foresee the presence of different sets of rollers that control this (not exclusively vertical) linear movement.

Many different approaches and techniques may be applied when constructing the different segments into a telescopic arm, some of which require that a very accurate positioning and adjustment of the rollers or bearings is to be ensured in order to obtain a smooth and accurate relative movement of the respective segments. The accurate positioning and adjustment of the rollers ensures that they continuously are in contact with a runner rail that guides the path of the rollers. A tight fit of the roller against the runner rails (which are both positioned between 2 subsequent arm segments) is required to ensure a taut operation, reduction of noise and reliable functioning over a long time.

However, the exact adjustment of the rollers relative to their respective runner rail or guiding system during the assembly step is not an easy process, as both the rollers and rails are fitted in the interspacing of two telescopic arm segments. This interspacing is not easily accessible with standard tools, and adjustment in any or other direction of the rollers to ensure a tight fit is not easily performed.

SUMMARY OF INVENTION

The present invention provides for a telescopic arm segment assembly as set out in claim 1, comprising at least one rolling element assembly, each comprising:
  two rolling elements, that in their own term each comprise a rolling element housing, two rollers that are rotatably fixed to one side of said rolling element housing, and two holes for aligning and subsequently fixing two threaded positioner bolts into corresponding mounting slits of a second segment of a telescopic arm, and a spring-loaded connecting element, connecting the two rolling elements such that the four rollers are clamped between the upper cover and lower termination of the runner rail,
  a set of concentrically arranged sliding arm segments, wherein a first segment comprises at least one runner rail with an upper cover and a lower termination arranged opposite to the upper cover, and wherein an second segment comprises at least four mounting slits for fixing said rolling element assembly by said threaded positioner bolts while being clamped in said runner rail, the relative positions of the positioner bolts in the mounting slits being determined by the clamping action of the spring-loaded connecting element. Specific examples and preferred embodiments are set out in the dependent claims.

In the context of this invention, a telescopic arm (often called a multi-stage arm) is a device that provides an exceptionally long output travel from a very compact retracted length. It consists of a number of retractable segments or tubes of progressively smaller diameters that are nested within each other. A telescopic arm can be a part of an X-ray imaging modality that supports, for instance, an X-ray source and allows it to be positioned with minimal force to another location (overhead the patient) when attached to a stationary base.

A telescopic arm segment is one of the retractable parts of a telescopic arm.

A telescopic arm segment assembly has, in the context of this invention, the equivalent meaning of the entire telescopic arm without the parts that connect the telescopic arm segment assembly to the supported device (such as the X-ray source), and without the parts that connect it to the device or structure that supports the telescopic arm segment assembly. The term thus refers only to the assembly comprising all necessary parts to provide the longitudinal travel movement.

The invention is advantageous in that the particular design of the telescopic arm segment assembly allows for an easy and optimal final adjustment of the segment positions relative to each other, and this without imposing special requirements on tooling or personnel. The automatic pre-alignment characteristics of the spring-loaded set of rolling elements forces the rollers into an optimal position with respect to the runner rail. The rolling elements are automatically forced into their desired position in the runner rail. The telescopic arm segments can then be brought into their final desired position (by bringing them in their concentric position), after which the fixing bolts can be tightened while it is ensured that the rollers remain into full contact with the runner rail.

An important advantage of the invention is that the final adjustment step saves time for the mechanic performing this step; it can be executed very fast thanks to the automatic spring-loaded adaption of the rolling elements in the running rail. Thanks to this, the application of this invention saves on installation cost of every system.

Another advantage of the invention is that the final adjustment result is highly repeatable, and thus increases the final alignment quality and result of the telescopic arm assemblies.

Further advantages and embodiments of the present invention will become apparent from the following description and drawings.

BRIEF DESCRIPTION OF DRAWINGS

FIG. 3 depicts two rolling elements [101], which comprise a rolling element housing [3] (that may consist of a metal sheet plate) in which at least two holes [5] are foreseen through which a bolt can be inserted. The rolling element housing [3] also has two rollers [2] and [2'] rotatably fixed to it by means of a fixed roller axis [7] allowing a smooth rotation of the rollers. It can be seen that the spring load of spring element [6] forces the outer rollers [2'] of the assembly against the upper cover [9] of the runner rail (the force being indicated as the downward pointing arrows against the outer rollers [2']), while the inner rollers [2] are forced against the lower termination [10] (the force being indicated by the upward pointing arrows against the inner rollers [2]). When the rolling element assembly is inserted in to the runner rails, the angle [40'] between the lines formed by the roller axes of both rolling elements [101] is noticeably smaller when compared to the angle when the spring is in rest state [40].

DESCRIPTION OF EMBODIMENTS

In the following detailed description, reference is made in sufficient detail to the above referenced drawings, allowing those skilled in the art to practice the embodiments explained below.

The invention concerns a particular telescopic arm segment assembly [200] that preferably finds its application in an X-ray device, and more particularly, a mobile X-ray device where it is customary to mount an X-ray source on an easily positionable arm that allows easy positioning of X-ray source.

The typical design of a telescopic arm involves the presence of at least two (but preferably more) concentric arm segments, which are designed such that they can move along their central axis; the axis is shared with all the involved segments. In other words, the central axes of the concentric segments coincide with each other. In many cases, four or five concentric segments are applied into one telescopic arm structure in order to provide the desired length of the extended arm. In all designs, the longitudinal (sliding) movement of the segments with respect to each other is supported by elements or specific features which are foreseen at the surfaces of the segments to allow the sliding interaction between the segments, or with assisting parts supporting the sliding interaction. It is the particular design of these features and parts that will determine the quality and tautness of the sliding movement of the telescopic arm.

The specific features and parts that may be applied to support the sliding movement are for instance a runner rail which is designed to guide a set of rollers that are attached to a next arm segment. Alternatively, different structures such as bearings (ball bearings) and guiding rails may also be applied.

Figure 1:
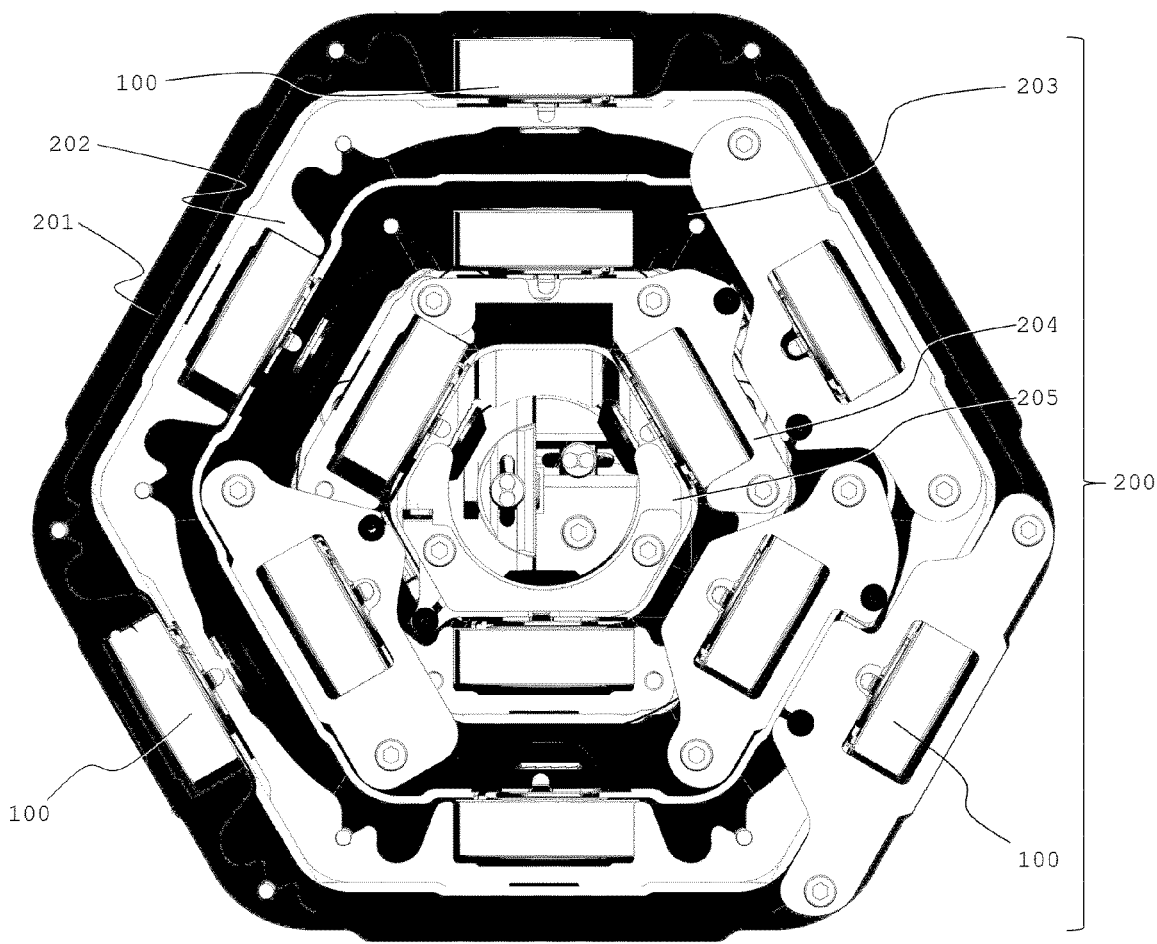
FIG. 1 gives a schematic overview of a cross-section of a telescopic arm assembly of the invention [200]. It depicts a telescopic arm assembly comprising five hexagonal concentric segments [201-205] of which the four innermost segments [202-205] can slide out of their respective neighbouring segment. It can be seen that in this embodiment, each hexagonal concentric segment (e.g. the outer segment [201]) comprises three rolling element assemblies [100] which are arranged in a triangular formation.
Figure 2:
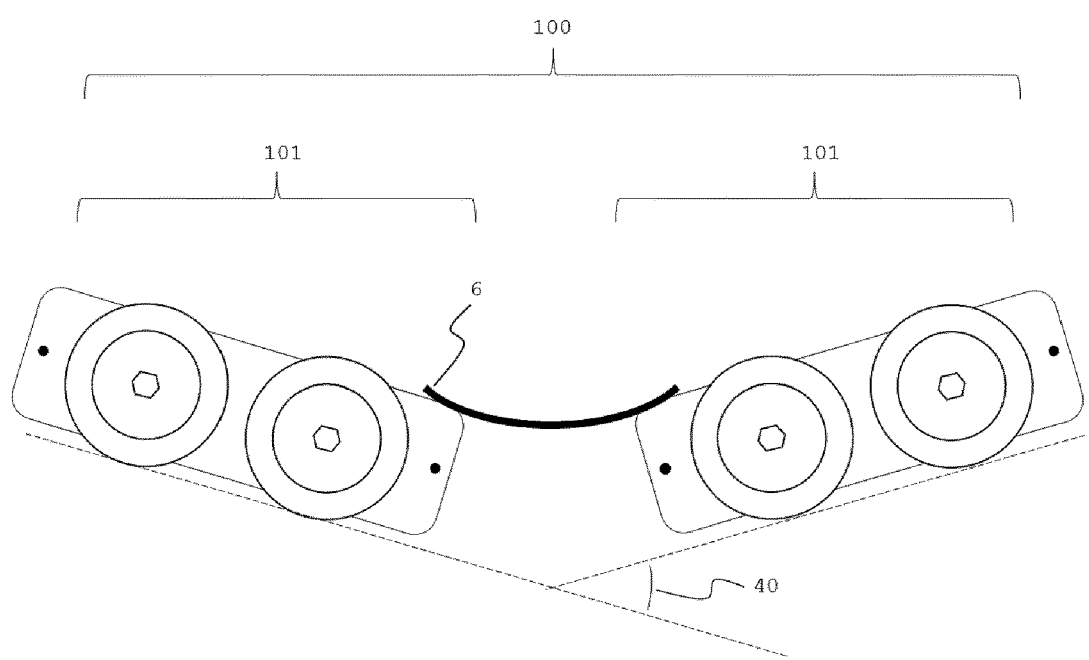
FIG. 2 gives an overview of the rolling element assembly [100] that is part of the telescopic arm assembly of the invention. The rolling element assembly [100] comprises three main components. It comprises two rolling elements [100] and a spring element [6] that connects both rolling elements [101]. The spring element [6] loads an angular momentum between both rolling elements forcing them into a position where an angle [40] represents the angle between the lines formed by the roller axes of both rolling elements [101]. When in their rest state, the spring element [6] is not loaded, and the angle [40] is therefore large.
Figure 3:
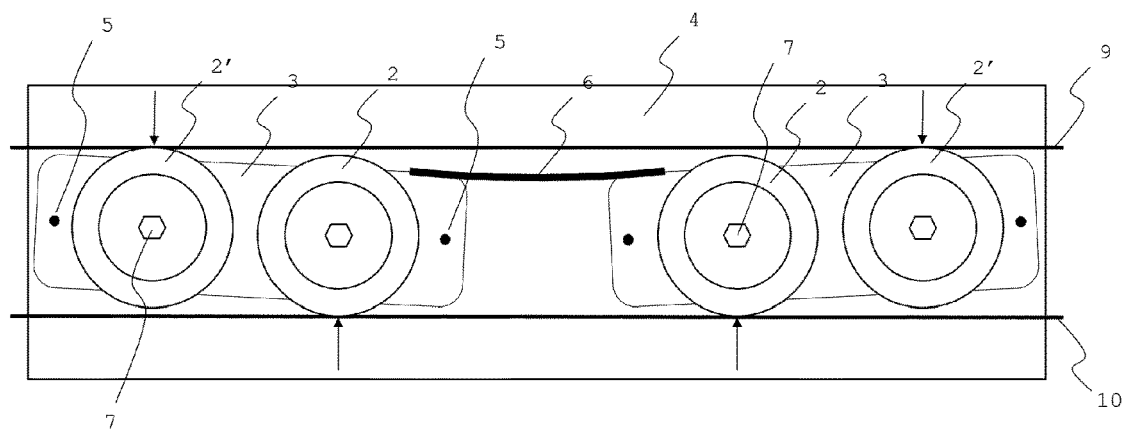
FIG. 3 depicts the same rolling element assembly [100] when mounted into its runner rail. The runner rail is represented in this drawing by the upper cover [9] and lower termination [10] of the runner rail. In this drawing the front cover [11] connecting both parts [9] and [10] of the runner rail is omitted, such that rolling element assembly [100] is visible (the front cover [11] of the runner rail is visible in FIG. 10). It has to be understood that the runner rail comprising the upper cover [9] and lower termination [10] is fixed to a different telescopic arm segment than the rolling element assembly [100]. The runner rail is fixed to a first telescopic arm segment via the front cover [11]. Whereas the rolling element assembly [100] is in fact fixed to a second telescopic arm segment surface indicated as [4].
Figure 4:
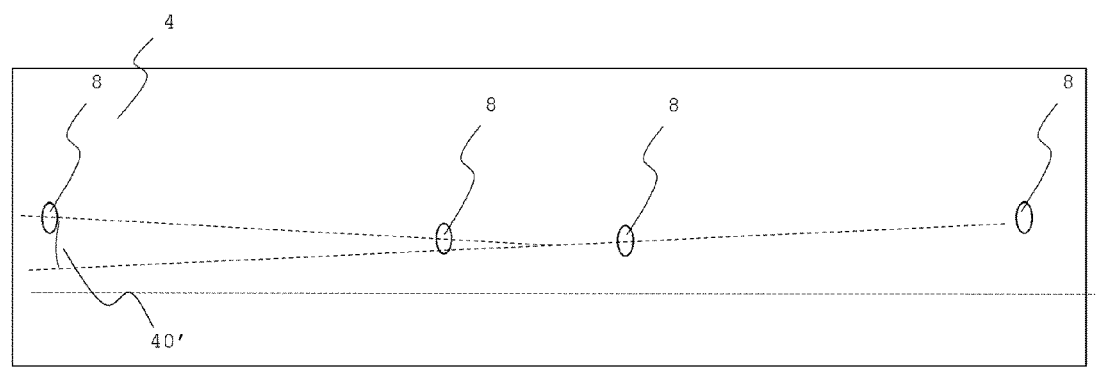
FIG. 4 represents the part of the second telescopic arm segment surface [4] to which the rolling element assembly [100] is to be fixed. The mounting slits [8] of the second segment [4] of the telescopic arm are pre-drilled into the segment surface material and allow the easy insertion of the bolts which are passed though the two holes [5] of the rolling element housing, even when the rolling element assembly [100] is inserted into the runner rail. The mounting slits [8] have a certain length such that the bolts are allowed a certain freedom of movement or "play" in a direction orthogonal to the direction of the runner rail. This allows the rolling element assembly to adjust to its optimal position (under the pressure of the spring element [6]) before then being fastened or fixed to the second telescopic arm segment surface [4], by fixing the bolts and nuts. In the depicted embodiment, the bolts that are used to fix the rolling element assembly to the second telescopic arm segment are inserted through the holes [5] that are drilled in to the rolling element housing. As can be seen in the image, the angle [40'] between the inclination of the respective slits is adjusted to the expected angle between the rolling elements [101] when inserted in the runner rail.
Figure 5:
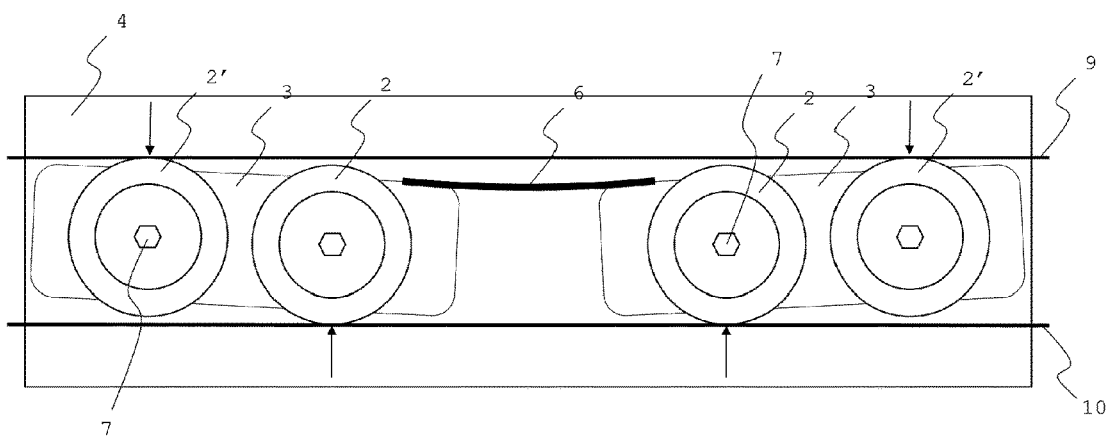
FIG. 5 depicts another embodiment of a same rolling element assembly [100] when mounted into its runner rail, with the difference that the bolts that are used to fix the rolling element assembly are in fact the axes [7] of the rollers [2] and [2'] mounted on the rolling elements [101].
Figure 6:
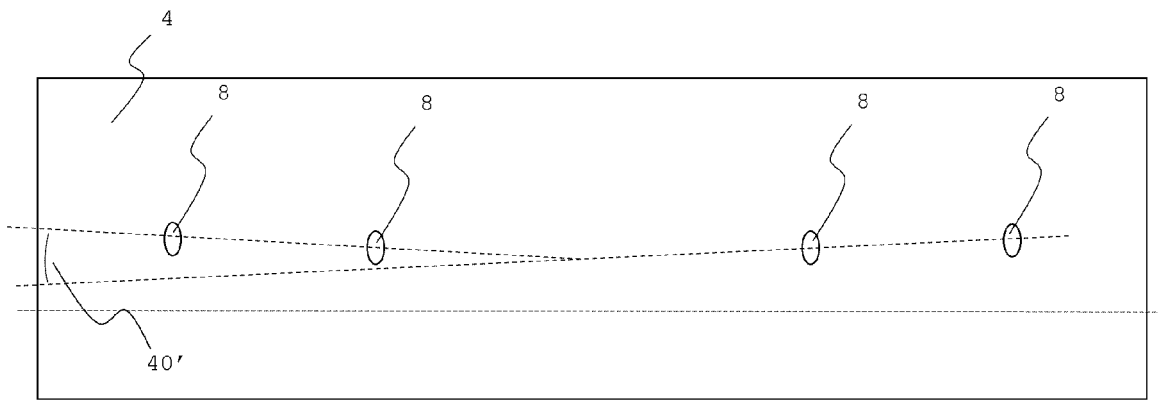
FIG. 6 depicts the corresponding second telescopic arm segment surface [4] to which the rolling element assembly [100] of FIG. 5 is to be fixed. The mounting slits [8] are positioned such that the roller axes fit the slits. As can be seen in the image, the angle [40'] between the inclination of the respective slits is adjusted to the expected angle between the rolling elements [101] when inserted in the runner rail.
Figure 7:
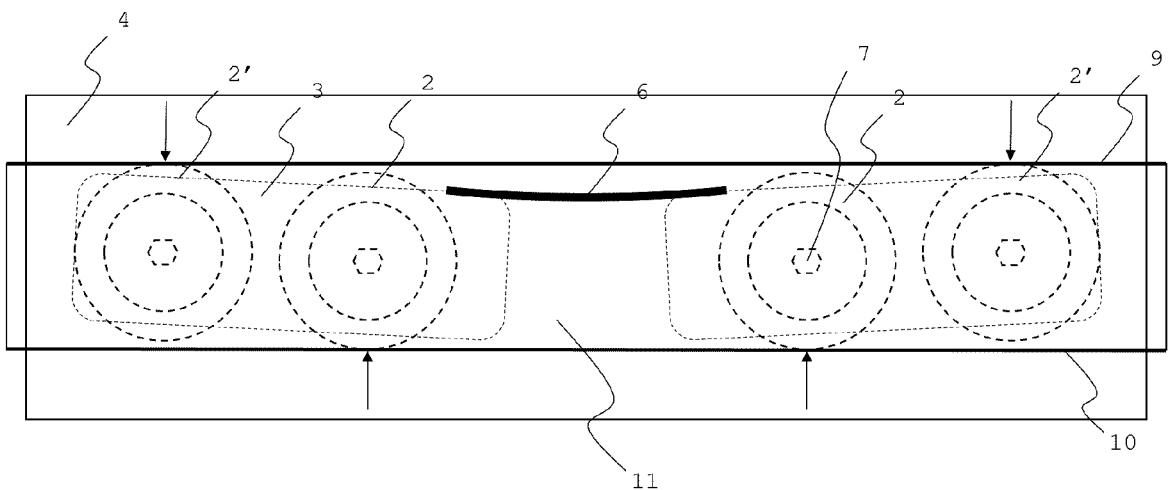
FIG. 7 represents the same embodiment of the invention as depicted in FIG. 5, but here the front cover of the running rail [11] is depicted, obscuring the rolling element assembly completely (which is suggested by the dotted lines used in the drawing). It is this front cover [11] that is mounted to the first telescopic arm segment (not visible in the drawing).
Figure 8:
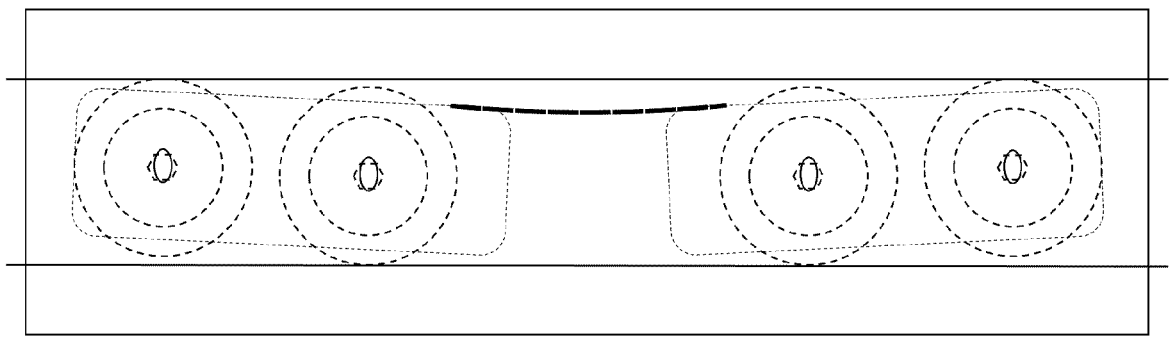
FIG. 8 is the same embodiment of the rolling element assembly as in FIG. 5, but seen from the opposite side of the entire structure. In this drawing, the mounting holes [5] in the surface of the second telescopic arm segment surface are visible, while the rest of the structure (including the rolling element assembly and the running rail) is not.
Figure 9:
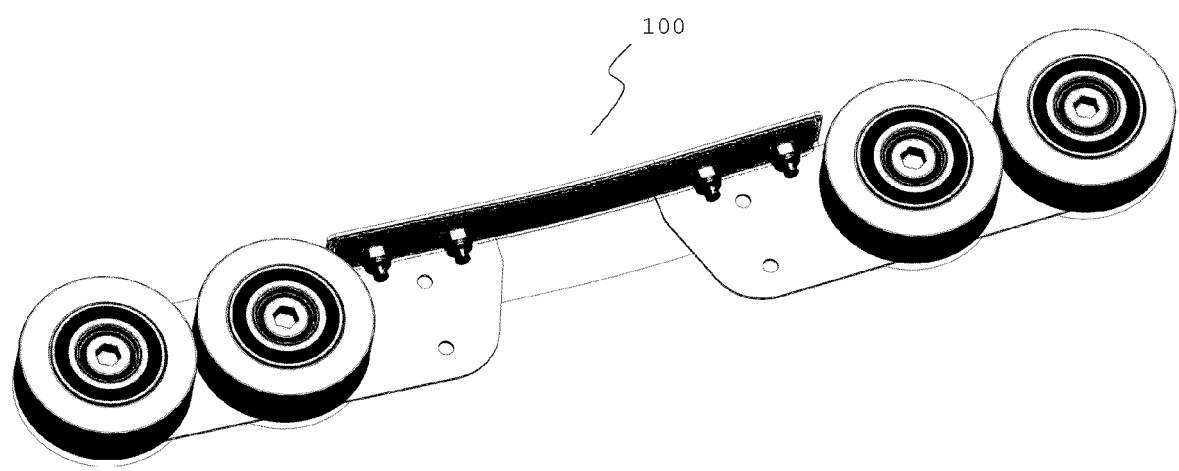
FIG. 9 is a 3-dimensional representation of an embodiment of a rolling element assembly [100].
Figure 10:
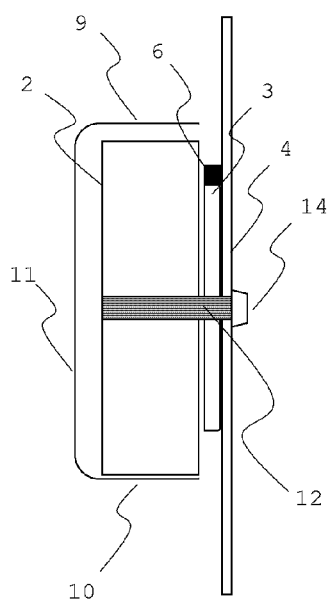
FIG. 10 is the lateral view of the same embodiment of the invention as depicted in FIG. 5, wherein the axis [12] of one of the rollers [2] serves also as the bolt that is used to fix the rolling element [3] to the second telescopic arm segment surface [4]. The bolt [12] is fastened using a nut [14] that fits the threads of the bolt. The drawing also illustrates the profile of an embodiment of the runner rail, which comprises the upper cover [9] and lower termination [10] (against which the rollers are pressed), and the front cover [11] of the running rail. The profile of the runner rail may adopt different shapes, but essentially should be able to guide the rollers in their linear movement along the rail.

The shape of the cross-sections of the telescopic arm segments should be such that it can host at least a pair of runner rails attached to opposite sides of each segment to provide for a stable sliding movement. The shape of the concentric cross-section of a segment may therefore be—for instance—a square or rectangle, or hexagonal, or even octagonal. As illustrated in FIG. 1, a preferred embodiment possesses an hexagonal shape, allowing it to fit three sets of runner rails and rolling element assemblies per segment. This configuration provides for a stable configuration supporting a very stable sliding movement.

At the least, a telescopic arm should be rigid and solid enough to support the weight of the supported device that is fixed at the end of the arm when fully extended. Moreover, the sliding movement of arm should be stable, free of noise and only minimal bending of the arm should occur. In order to achieve this, there should be minimal tolerance or play between the moving and sliding parts between the concentric arm segments, meaning that a very precise assembly and fixation of these moving and sliding parts is required. It can be easily understood that while the involved moving and sliding parts are mounted in between the interspace of two subsequent arm segments, the final alignment and fastening of these components can be very cumbersome and difficult.

The particular design of the rolling element assembly [100] of the invention allows for a rigid movement of the arm's segments during operation, and at the same time allows for an easy correct fastening of the involved telescopic arm segments during the assembly of the telescopic arm.

The rolling element assembly [100] is designed as a carriage, and comprises three main components: two rolling elements [101] that are connected to each other via a spring element [6]. The spring element [6] loads an angular momentum between both rolling elements forcing them into a position where an angle [40] represents the angle between the lines formed by the roller axes of both rolling elements [101]. The spring element [6] in fact applies a force on the two centrally located rollers [2] of the rolling element assembly [100] and presses them downward to make firm contact with the lower termination [10] of the runner rail. At the same time, the spring element applies an opposite force on the two peripherally located rollers [2'] pushing them upwards against the upper cover [9] of the runner rail. Both forces in fact "squeeze" the rolling element assembly [100] in its totality firmly between both covers of the runner rail, ensuring a tight and accurate alignment of the rolling element assembly with the runner rail trajectory.

The spring element [6] can be implemented as an elastic piece of bended metal that stores mechanical energy when being brought into a straight shape. The spring element may be a flat spring made of spring steel, and is attached to both rolling element [101] of the rolling element assembly. The spring element may be attached to the rolling element by means of a weld, a set of screws, bolts or other means.

In the context of this invention, when considering the relative positions of two neighbouring arm segments and referring to a first and second arm segment of the telescopic arm, the "first segment" is referred to as the outer segment of two concentric segments, while the "second segment" is the segment that will be mounted inside the "first segment".

In a preferred embodiment, the rolling element assembly [100] is intended to be fixed to the second (innermost) segment of the two concentric arm segments, such that the rollers of the assembly can interact with the runner rail that is part of the first (outermost) arm segment. The rolling element assembly [100] therefore should be pre-mounted to the second arm segment. Pre-mounting in this context means that the (at least two) bolts are inserted through or screwed into the holes [5] of the rolling elements, the same bolts being driven loosely through the mounting slits [8] of the second telescopic arm segment [4]. The pre-mounting of the rolling element assembly can be easily done to the surface of the second arm segment while this surface is still easily accessible for mounting while the segment is not inserted into the second arm segment.

Since the bolts are not tightened or fastened yet at this point, there is freedom for movement of the bolts in the mounting slits [8]. Preferably, the bolts are fixed or screwed into the holes [5] of the rolling elements, such that the movement of the rolling elements [101] is limited by the movement of the bolts within the tolerances of the mounting slits [8]. This limited linear movement of the shafts of the bolts in the mounting slits allows that the rolling elements [101] fully and automatically can align to the runner rail under the influence of the spring element [6] as explained above. It is only after this automatic alignment of the rollers [2][2'] (and consequently of the rolling elements [101]) that the rolling elements are to be fully fixed to the second arm segment by tightening the bolts such that no further relative movement of the bolts is possible in the mounting slits [8]. After this final tightening step, the assembly of the second segment inside the first arm segment is complete. This final assembly ensures the fixation of the rollers in the optimal position with respect to the second segment and at the same time assures the fixation of the rollers in the optimal position with respect to the upper [9] and lower [10] covers of the runner rail (that is part of the first arm segment).

In another embodiment of this invention, the configuration of the running rail is inverted, such that the running rail is now part of the second arm segment (rather than the first arm segment). In this configuration, the rolling element assembly should be fixed to the first segment.

In another embodiment, the bolts that are fixing the two rolling elements [101] of the rolling element assembly [100] to the surface of the second arm segment are substituted with the axes of the rollers [2][2'] which then serve at the same time as fixation bolts. In this embodiment, the holes [5] in the rolling element housing [3] are not separately foreseen, but are the same holes that are used by the axes of the rollers. Evidently, the positions of and relative distances between the mounting slits [8] will be different when compared to the main preferred embodiment illustrated above.

While it is paramount that the rolling element assembly is fixed correctly (i.e. making sure that the rollers entirely in parallel with the concentric axis of the first arm segment, the spring element will ensure that—once the rollers of the rolling element assembly are inserted into the running rail—the rollers will be assume their intended positions.

After the rolling element assembly is mounted in the correct position, it can be easily inserted into the second arm segment by fitting the rollers of the rolling element assembly into the runner rail of the second arm segment.

The invention claimed is:

1. A telescopic arm segment assembly, comprising a rolling element assembly comprising:
   two rolling elements, each comprising:
      a rolling element housing,
      two rollers that are rotatably fixed to one side of said rolling element housing, and
      two holes for aligning and subsequently fixing two threaded positioner bolts into corresponding mounting slits of a second segment of a telescopic arm, and
   a spring-loaded connecting element, connecting the two rolling elements, and comprising a set of concentrically arranged sliding arm segments comprising a first segment and a second segment,
   wherein the first segment comprises at least one runner rail with an upper cover and a lower termination arranged opposite to the upper cover,
   wherein the second segment comprises at least four mounting slits for fixing said rolling element assembly by said threaded positioner bolts while being clamped in said runner rail, the relative positions of the positioner bolts in the mounting slits being determined by the clamping action of the spring-loaded connecting element, and
   wherein the spring-loaded connecting element connects the two rolling elements such that the four rollers are clamped between the upper cover and lower termination of the at least one runner rail.

2. The telescopic arm segment assembly of claim 1, wherein the rollers on the rolling elements have axes which also serve as the threaded positioner bolts.

3. The telescopic arm segment assembly of claim 2, wherein the sliding arm segments have a squared, a hexagonal, an octagonal, or a decagonal cross-section.

4. The telescopic arm segment assembly of claim 1, wherein the sliding arm segments have a squared, a hexagonal, an octagonal, or a decagonal cross-section.

5. The telescopic arm segment assembly of claim 4, wherein the positioner bolts are threaded screws that are fixed on the surface of the rolling elements by a nut, and extend into the corresponding mounting slits of the second segment of a telescopic arm.

6. The telescopic arm segment assembly of claim 1, wherein the positioner bolts are threaded screws that are fixed on the surface of the rolling elements by a nut, and extend into the corresponding mounting slits of the second segment of a telescopic arm.

7. The telescopic arm segment assembly of claim 2, wherein the positioner bolts are threaded screws that are fixed on the surface of the rolling elements by a nut, and extend into the corresponding mounting slits of the second segment of a telescopic arm.

8. The telescopic arm segment assembly of claim 3, wherein the positioner bolts are threaded screws that are fixed on the surface of the rolling elements by a nut, and extend into the corresponding mounting slits of the second segment of a telescopic arm.

* * * * *